(12) United States Patent  
Gregorian

(10) Patent No.: US 9,999,737 B2  
(45) Date of Patent: Jun. 19, 2018

(54) ENDOTRACHEAL TUBE WITH RADIOPAQUE DISTAL END MARKER

(76) Inventor: Felix Gregorian, North Chelmsford, MA (US)

( * ) Notice: Subject to any disclaimer, the term of this patent is extended or adjusted under 35 U.S.C. 154(b) by 1086 days.

(21) Appl. No.: 12/051,885

(22) Filed: Mar. 20, 2008

(65) Prior Publication Data

US 2008/0230070 A1    Sep. 25, 2008

Related U.S. Application Data

(60) Provisional application No. 60/895,794, filed on Mar. 20, 2007.

(51) Int. Cl.
  *A61M 16/04* (2006.01)

(52) U.S. Cl.
  CPC ......... *A61M 16/04* (2013.01); *A61M 16/0411* (2014.02); *A61M 16/0434* (2013.01); *A61M 16/0488* (2013.01); *A61M 2205/32* (2013.01)

(58) Field of Classification Search
  CPC .......... A61M 16/0488; A61M 16/0497; A61M 2205/32
  USPC ....... 128/207.14–207.18, 200.26; 604/93.01, 604/96.01; 606/108
  See application file for complete search history.

(56) References Cited

U.S. PATENT DOCUMENTS

| | | | |
|---|---|---|---|
| 4,502,482 A | 3/1985 | DeLuccia et al. | |
| 4,588,399 A | 3/1986 | Nebergall et al. | |
| 4,690,138 A * | 9/1987 | Heyden | A61M 16/04 116/324 |
| 5,020,534 A | 6/1991 | Pell et al. | |
| 5,437,290 A * | 8/1995 | Bolger et al. | 128/898 |
| 6,055,984 A * | 5/2000 | Brain | A61M 16/04 128/207.14 |
| 6,723,113 B1 * | 4/2004 | Shkolnik | 606/194 |
| 2002/0096177 A1 | 7/2002 | Toti et al. | |
| 2004/0084050 A1 | 5/2004 | Baran | |
| 2005/0149060 A1 | 7/2005 | Thorstenson et al. | |
| 2005/0267409 A1 | 12/2005 | Shkolnik | |
| 2007/0017527 A1 * | 1/2007 | Totz | 128/207.15 |

OTHER PUBLICATIONS

International Prelminary Examination Report of co-pending PCT application No. PCT/US2008/057612 dated Oct. 1, 2009.

* cited by examiner

*Primary Examiner* — Valerie L Woodward
(74) *Attorney, Agent, or Firm* — Timothy Marc Shropshire; Eric Brandon Lovell; Garrett James O'Sullivan

(57) ABSTRACT

An endotracheal tube comprising a tubular member including a distal portion and a distal end, a radiopaque stripe extending longitudinally along the distal portion of the tubular member, and a radiopaque ring encircling at least a portion of the tubular member at the distal end. The radiopaque ring may be a complete oval, a substantial arc of an oval, or a series of arcs of an oval.

20 Claims, 3 Drawing Sheets

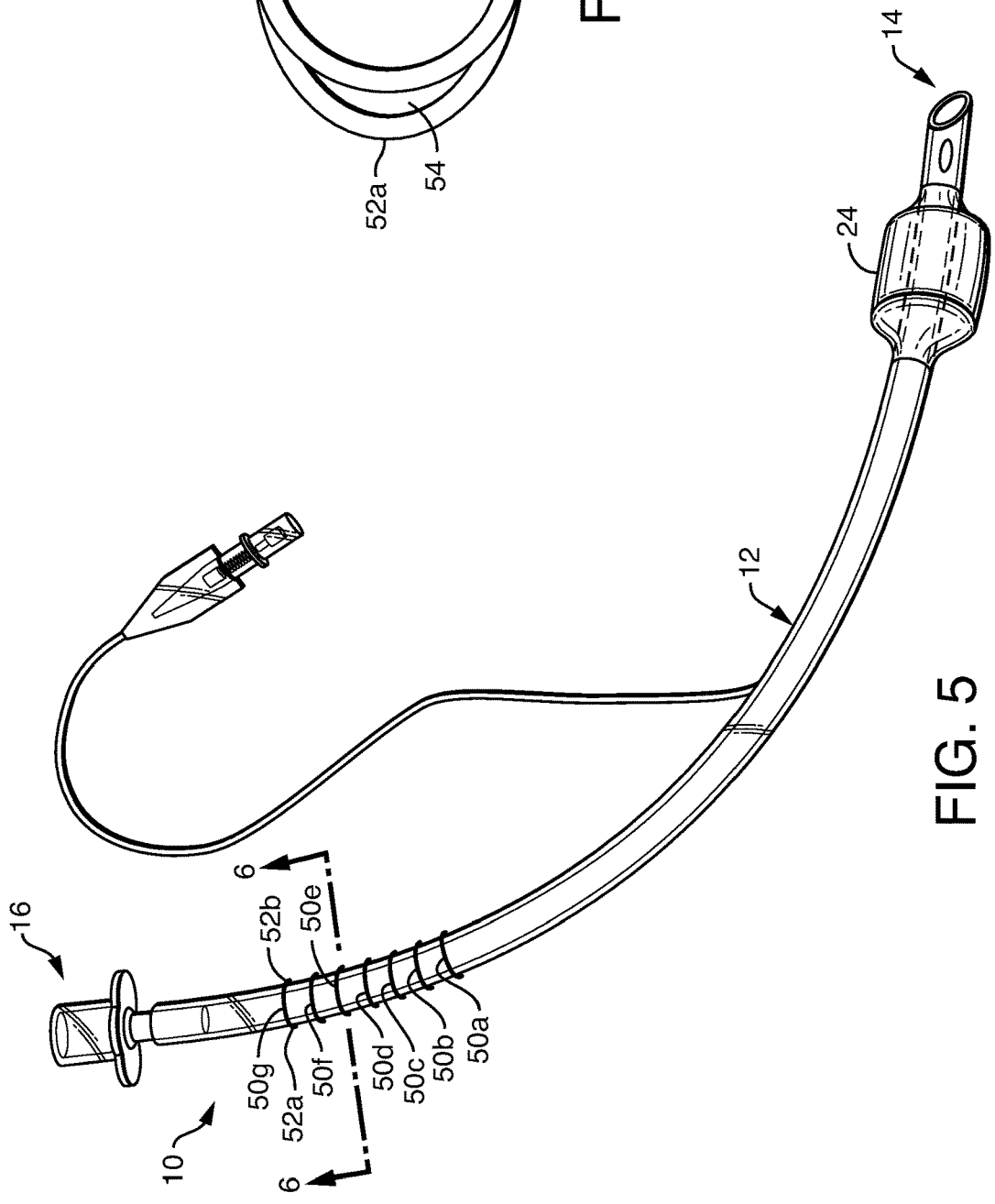

ENDOTRACHEAL TUBE WITH RADIOPAQUE DISTAL END MARKER

CROSS-REFERENCES TO RELATED APPLICATIONS

The applicant wishes to claim the benefit of U.S. Provisional Patent Application No. 60/895,794, filed Mar. 20, 2007 for ENDOTRACHEAL TUBE IMPROVEMENTS in the name of Felix Gregorian.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

The present invention relates to medical devices, more particularly, to endotracheal tubes.

DESCRIPTION OF RELATED ART

Endotracheal tubes (ETTs) are used for airway management and patency for various medical situations. These particular patient treatment times usually are either chosen voluntarily (pending a major surgery) or in emergency conditions (like an accident requiring establishment of an airway, or a code blue, where patient is in a compromised situation and in danger of losing his/her life). It is in these difficult conditions that a medical professional intubates the patient.

One problem with endotracheal tubes is in determining when the tube has been inserted the proper distance into the patient's trachea. Correct positioning of an ETT is usually defined as the placement of the tube within the trachea approximately 3 cm to 5 cm above the carina. Current ETTs have a radiopaque strip in the ETT wall that extends longitudinally to the proximal end. This radiopaque strip is generally visible as a line on an x-ray. The problem is that sometimes the line is not visible due to orientation of the ETT or the x-ray machine. In other cases, apertures through the ETT wall, such as a Murphy Eye, interrupt the line, and the resulting short line at the end of the ETT is not easily seen.

Another placement issue is that if the ETT is not inserted far enough into the trachea, the cuff abuts the vocal cords, possibly causing damage to the vocal cords and not permitting an adequate seal around the ETT.

Another issue is knowing how far the ETT has been inserted during the insertion process. Unless x-rays are taken continuously as the ETT is being inserted, it is not known with any accuracy how far the ETT has been inserted.

Another issue is securing the ETT to a patient after intubation. Once an ETT is in position, tape is used to secure the ETT to the patient to prevent movement relative to the patient. If the tape is not secured properly so that it adheres to the ETT, it is possible that the ETT can move over time.

Another issue is that the air outlet is in the center of the end of the tube. Consequently, air blown into the tube is not directed into the left or right bronchus, but at the joint between them. If the patient is missing a lung, meaning that the associated bronchus is terminated, the air from the ETT may put an inordinate amount of pressure on the terminated bronchus, causing injury.

BRIEF SUMMARY OF THE INVENTION

An object of the present invention is to provide an endotracheal tube, the end of which is easily visible via x-ray at all angles during placement in the trachea.

Another object is to provide an endotracheal tube where the location of the ETT cuff is easily visible via x-ray at all angles during placement in the trachea.

Yet another object is to provide an endotracheal tube that is marked to easily show how far the ETT has been inserted into the trachea.

Yet another object is to provide an endotracheal tube that directs air into each bronchus rather than between them.

The several inventions described in the present specification are for use with an endotracheal tube, which typically includes a plastic tube with proximal opening for attaching a ventilator, a distal opening. A cuff retains the ETT in position when inflated and a pilot balloon is used to inflate the cuff. A radiopaque strip is adhered to or imbedded longitudinally in the tube.

One invention extends the radiopaque strip to encircle the distal opening in a radiopaque ring that shows up in an x-ray as a line or oval at the end of the radiopaque line, thereby making the end of the ETT much more visible.

Another invention brackets the cuff above and below with a pair of radiopaque rings, making the cuff location visible on an x-ray.

Another invention is the addition of annular markings on ETT. The markings are at known distances from the distal end of the ETT so that the distance that the ETT has been inserted is known as the ETT is inserted.

Another invention is the addition of flat attachment eyelets to the ETT. When the ETT secured after intubation, the tape or other securing mechanism is threaded through the aperture of one or more of the eyelets.

Another invention consists of closing the distal end and adding one or two openings in the tube wall adjacent to the distal end on opposite sides of the plane of curvature so that the openings are adjacent to the patient's left and right bronchi after intubation. The exiting air is directed straight into both bronchi, rather than impinging directly on the carina. Further, one of the openings can be closed in the event that air is not desired into one of the bronchi. The radiopaque strip can be extended to encircle the closed, distal end in a radiopaque ring that shows up in an x-ray as a line or oval.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein:

FIG. 5 is a side view of an endotracheal tube showing the ETT attachment invention;

FIG. 6 is an enlarged, cross-sectional view of a flat eyelet of FIG. 5 taken at 6-6;

DETAILED DESCRIPTION OF THE INVENTION

Figure 1:
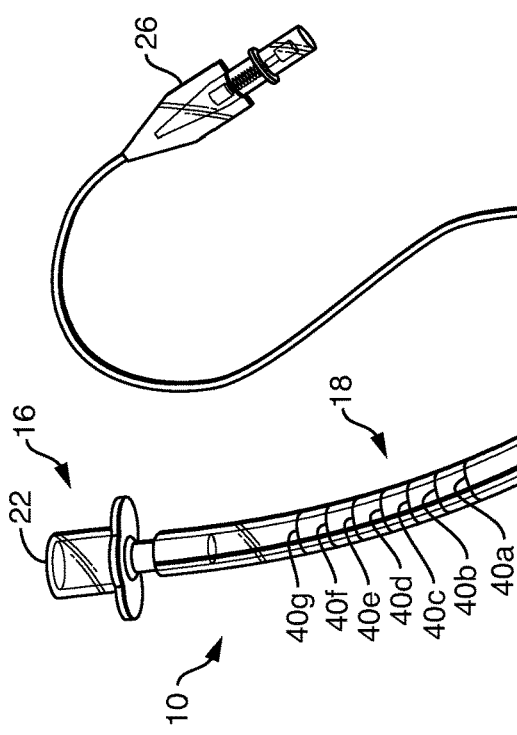
FIG. 1 is a side view of an endotracheal tube showing the radiopaque marker invention.

FIG. 1 shows an ETT 10 implementing the radiopaque marker invention describe herein. The typical ETT 10 is comprised of a flexible, plastic tubular member 12 with an opening 20 at the distal end 14 and an opening 22 at the proximal end 16. A ventilator or other breathing apparatus is connected to the proximal end opening 22. Adjacent to the distal end 14 is a cuff 24, an inflatable balloon, that, when inflated, retains the ETT 10 in position in the airway and closes the airway outside of the ETT 10. The pilot balloon 26 is used to inflate the cuff 24. An opening 28 in the side of the tubular member 12 adjacent to the proximal end, also called a Murphy Eye, prevents respiratory obstruction in the event the proximal opening 20 becomes plugged.

In order for the ETT to be visible in an x-ray, it is known in the art to incorporate a radiopaque stripe 30 longitudinally in the tubular member 12 along at least the distal portion 38 of the tubular member 12 and end at or near the distal end 14. The radiopaque stripe 30 may be made of any of the known materials that are used for this purpose and can be adhered to or imbedded in the tubular member 12. The circumferential location of the strip 30 may be anywhere on the ETT. For example, as shown in FIG. 1, the stripe 30 is on the back of the ETT, that is, on the outside of the curve of the tubular member 12. Alternatively, the stripe 30 is on the front, that is, on the inside of the curve of the tubular member 12. Alternatively, the stripe 30 is on the side of the tubular member 12. The radiopaque material, as the name suggests, enables the ETT to be seen using an x-ray machine so that the ETT can be placed correctly. As described above, there are instances when the radiopaque stripe 30 cannot be seen.

Figure 3:
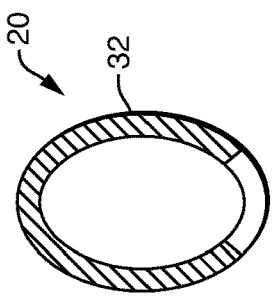
FIG. 3 is an end view of the endotracheal tube of FIG. 1 showing a second embodiment of the radiopaque ring.
Figure 4:
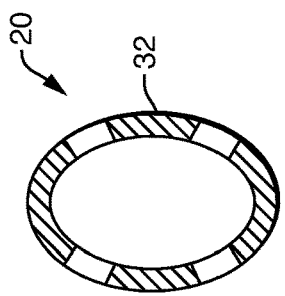
FIG. 4 is an end view of the endotracheal tube of FIG. 1 showing a third embodiment of the radiopaque ring.
Figure 2:
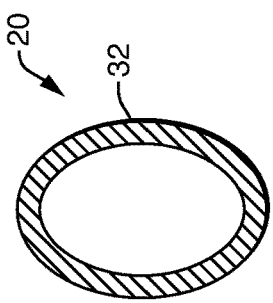
FIG. 2 is an end view of the endotracheal tube of FIG. 1 showing one embodiment of the radiopaque ring.

One invention described herein and shown in FIG. 1 the radiopaque stripe 30 ends at a radiopaque ring 32 that partially or completely encircles the distal end 14, preferably at the opening 20. The present invention contemplates at least three configurations of the ring 32. In one configuration, the ring 32 is complete, that is, it is a complete oval about the distal end 14, as in FIG. 2. The term, "oval", includes the special case of a circle. In another configuration, the ring 32 is only a substantial arc of an oval about the distal end 14, as in FIG. 3. In another configuration, the ring 32 is a series of arcs of an oval about the distal end 14, as in FIG. 4. The radiopaque ring 32 will show up in an x-ray as a line that is generally perpendicular to the radiopaque stripe 30 or an arc or oval at the end of the radiopaque stripe 30, thereby marking the distal end of the ETT 10 and making it much more visible and not dependent on the orientation of the ETT.

Optionally, the radiopaque ring idea is extended to include a radiopaque ring 34 that partially or completely encircles the tubular member 12 at the proximal side of the cuff 24 and another radiopaque ring 36 that partially or completely encircles the tubular member 12 at the distal side of the cuff 24. As described above, incorrect placement of the ETT 10 can cause damage to the vocal cords and an inadequate seal when the cuff 24 is inflated. Radiopaque rings 34, 36 that bracket the cuff 24 makes the cuff location visible on an x-ray.

In another invention, shown in FIG. 1, annular markings 40a-40g (collectively, 40) are printed on or embedded in the proximal portion 18 of the ETT 10. The markings 40 are visible marks either on the outside of the tubular member 12 or embedded within the tubular member 12. The markings 40 are at known distances from the distal end 14 of the ETT 10 so that the distance that the ETT 10 has been inserted can be calculated as the ETT 10 is inserted. In one example, the marks 40 are at 18, 20, 22, 24, 26, 28, and 30 centimeters from the proximal end 14.

In another invention, shown in FIGS. 5 and 6, flat attachment eyelets 50a-50g (collectively, 50) are added to the ETT 10. The eyelets 50 are permanently secured to the ETT 10 in whatever manner is appropriate. In one arrangement, the flat eyelets 50 are located in the same positions as the annular markings 40 describe above. When the ETT 10 secured after intubation, the tape or other securing mechanism is threaded through the aperture 54 of one or more of the flat eyelets 50 to prevent the tape from sliding longitudinally along the ETT, thereby holding the ETT in place. The present invention contemplates that the eyelets 50 may consist of one, two, or more loops 52 at each longitudinal location. In the example of FIGS. 5 and 6. There are two such loops 52a, 52b at each location.

Figure 7:
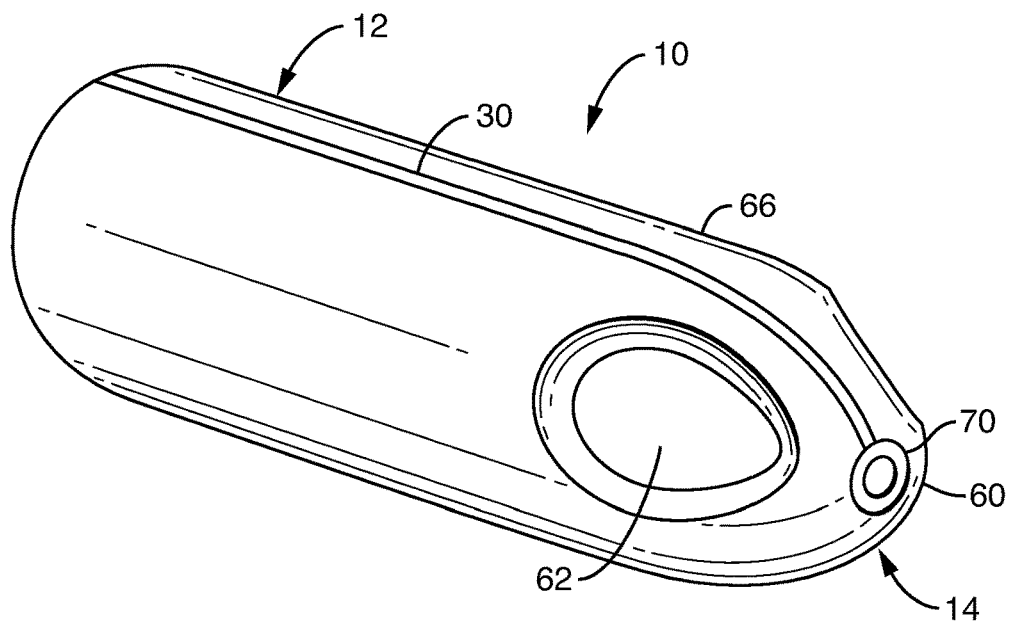
FIG. 7 is a perspective view of an endotracheal tube showing the dual opening invention.
Figure 8:
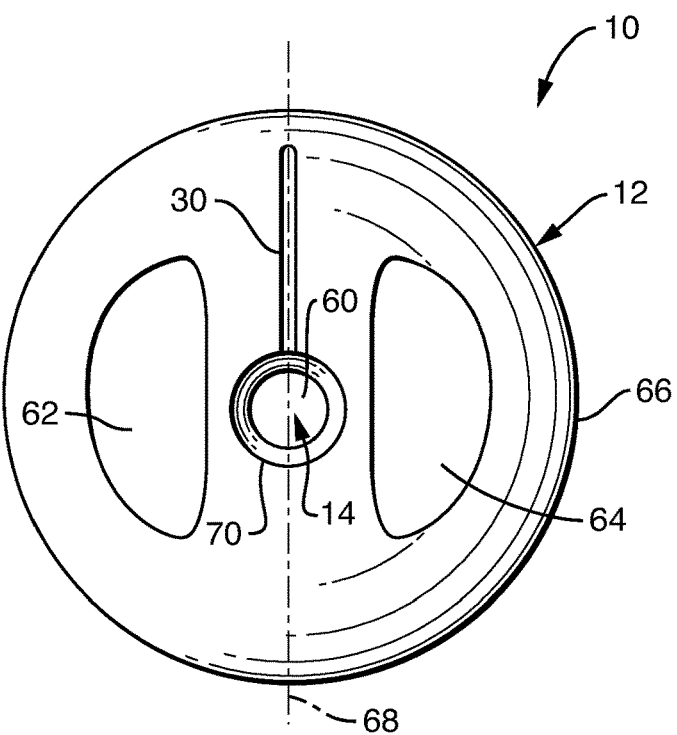
FIG. 8 is an end view of the endotracheal tube of FIG. 7.

Another invention described herein is shown in FIGS. 7 and 8. The standard ETT has a single opening at the distal end 14. The present invention closes the distal end 14, as at 60, and adds one or two openings 62, 64 in the tube wall 66 adjacent to the distal end 14. The openings 62, 64 are round, oval, or other shape that is appropriate. The closed end 60 is formed into a small rounded tip that is stiff, yet soft enough that it does not damage the carina if it should make incidental contact.

An ETT 10 curves in a plane 68 so that it fits more easily in a patient's airway. The openings 62, 64 are located on opposite sides of the plane of curvature 68 so that the openings 62, 64 are adjacent to the patient's left and right bronchi after intubation. The openings 62, 64 provide at least two benefits. First, the air exiting the distal end 14 of the ETT 10 does not impinge directly on the carina, which can cause damage if the air pressure is high enough. Second, the exiting air is directed straight into both bronchi, rather than having to be deflected by the carina.

Further, having two openings 62, 64 directly to the bronchi permits one of the openings to be closed in the event that air is not desired into a bronchus in the event, for example, that the lung is missing or injured. In one configuration, the ETT 10 is manufactured with only one of the openings 62, 64, with the other opening location being closed. Consequently, there will be two versions, one with only the right side opening 62 and one with only the left side opening 64. Alternatively, the openings 62, 64 are manufactured with punch-out or pull-out plugs that can be removed prior to intubation. For normal usage, both plugs are removed. In special cases, only the plug in the desired opening is removed. In one embodiment, the plug has a tab that is pulled for removal so that the plug does not become lodged inside the ETT.

The radiopaque ring invention described above can be implemented in the dual-opening invention as shown in FIGS. 7 and 8. The radiopaque stripe 30 extends between the two openings 62, 64 and forms a ring 70 that partially or completely encircles the closed distal end 60. As with the ring 32 described above, the ring 70 can have various configurations, including a complete oval, an arc of an oval, or a series of arcs of an oval. Depending on the size of the closed end 60 and position of the ETT 10 in the patient, the ring 70 may appear as a line, arc, circle, oval, or large dot in an x-ray, any one of which will clearly show the distal end of the ETT.

Thus it has been shown and described an endotracheal tube which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

I claim:

1. An endotracheal tube comprising:
   a) a continuous tubular member including a proximal end, a distal portion, and a distal end, wherein the continuous tubular member includes a pair of opposed openings adjacent to the distal end, wherein the distal end is closed, and wherein the distal end is rounded;
   b) a radiopaque stripe extending longitudinally along the distal portion of the continuous tubular member to the distal end; and
   c) a radiopaque ring at least partially encircling the continuous tubular member at the distal end, wherein the radiopaque ring identifies a terminus of the distal end, and wherein the radiopaque stripe contacts the radiopaque ring,
   wherein the radiopaque ring is more distal than the pair of opposed openings.

2. The endotracheal tube of claim 1, wherein the radiopaque ring is a complete oval about the continuous tubular member.

3. The endotracheal tube of claim 1, wherein the radiopaque ring is a substantial arc of an oval about the continuous tubular member.

4. The endotracheal tube of claim 1, further comprising:
   a) an inflatable balloon cuff in the distal portion;
   b) a radiopaque ring at least partially encircling the continuous tubular member adjacent to a proximal end of the cuff; and
   c) a radiopaque ring at least partially encircling the tubular member adjacent to a distal end of the cuff.

5. The endotracheal tube of claim 1, further comprising a plurality of attachment eyelets, wherein each attachment eyelet comprises:
   a) a central aperture that circumferentially engages the continuous tubular member; and
   b) at least one loop extending from the central aperture, wherein each attachment eyelet is permanently positioned at a unique longitudinal position along a proximal portion of the continuous tubular member.

6. The endotracheal tube of claim 5, further comprising a plurality of annular markings positioned along the proximal portion, wherein each of the attachment eyelets is aligned with a corresponding annular marking, wherein each of the annular markings is positioned at a known distance from the distal end.

7. The endotracheal tube of claim 6, wherein the annular markings are positioned at 18, 20, 22, 24, 26, 28, and 30 centimeters from the distal end.

8. The endotracheal tube of claim 1, further comprising:
   a) a first plug positioned within a first opening of the pair of opposed openings; and
   b) a second plug positioned within a second opening of the pair of opposed openings,
   wherein the first plug and the second plug are removably attached to the tubular member, wherein at least the first plug or the second plug is removed prior to using the endotracheal tube.

9. An endotracheal tube comprising:
   a) a tubular member including at least a first opening adjacent to a distal end of the tubular member, wherein the distal end is closed and rounded, and wherein an opposite proximal end is open;
   b) a radiopaque marker at least partially encircling the distal end, wherein the radiopaque marker identifies a terminus of the distal end, and wherein the radiopaque marker is more distal than the first opening; and
   c) a plurality of attachment eyelets, wherein each attachment eyelet comprises:
      i) a central aperture that circumferentially engages the tubular member; and
      ii) at least one loop extending from the central aperture, wherein each attachment eyelet is permanently positioned at a unique longitudinal position along a proximal portion of the tubular member.

10. The endotracheal tube of claim 9, further comprising a plurality of annular markings positioned along the proximal portion, wherein each of the attachment eyelets is aligned with a corresponding annular marking, wherein each of the annular markings is positioned at a known distance from the distal end.

11. The endotracheal tube of claim 10, wherein the annular markings are positioned at 18, 20, 22, 24, 26, 28, and 30 centimeters from the distal end.

12. The endotracheal tube of claim 9, further comprising a radiopaque stripe extending longitudinally along a distal portion of the tubular member to the distal end, wherein the radiopaque stripe contacts the radiopaque marker.

13. The endotracheal tube of claim 9, further comprising:
   a) an inflatable balloon cuff positioned in a distal portion of the tubular member, adjacent to, and proximally of, the first opening;
   b) a radiopaque marker at least partially encircling the tubular member adjacent to a proximal end of the cuff; and
   c) a radiopaque marker at least partially encircling the tubular member adjacent to a distal end of the cuff.

14. The endotracheal tube of claim 9, wherein the tubular member further includes a second opening adjacent to the distal end, wherein a distance between the first opening and the distal end is equal to a distance between the second opening and the distal end.

15. The endotracheal tube of claim 14, wherein the first opening and the second opening are positioned directly opposite of one another.

16. The endotracheal tube of claim 14, further comprising a plurality of annular markings positioned along the proximal portion, wherein each of the attachment eyelets is aligned with a corresponding annular marking, wherein each of the annular markings is positioned at a known distance from the distal end.

17. The endotracheal tube of claim 16, wherein the annular markings are positioned at 18, 20, 22, 24, 26, 28, and 30 centimeters from the distal end.

18. The endotracheal tube of claim 14, further comprising:
   a) an inflatable balloon cuff positioned in a distal portion of the tubular member, adjacent to, and proximally of, the first opening and the second opening;

b) a radiopaque marker at least partially encircling the tubular member adjacent to a proximal end of the cuff; and c) a radiopaque marker at least partially encircling the tubular member adjacent to a distal end of the cuff.

19. The endotracheal tube of claim 14, further comprising:

a) a first plug positioned within the first opening; and b) a second plug positioned within the second opening, wherein the first plug and the second plug are removably attached to the tubular member, wherein at least the first plug or the second plug is removed prior to using the endotracheal tube.

20. The endotracheal tube of claim 9, further comprising at least one plug, wherein each plug uniquely corresponds to one of each opening adjacent to the distal end of the tubular member, wherein each plug is positioned within its corresponding opening and is removably attached to the tubular member, wherein at least one plug is removed prior to using the endotracheal tube.

* * * * *